(12) United States Patent
Yoshimoto et al.

(10) Patent No.: US 10,329,231 B2
(45) Date of Patent: *Jun. 25, 2019

(54) EPOXY COMPOUND, METHOD FOR PRODUCING THE SAME, EPOXY RESIN COMPOSITION, AND CURED PRODUCT THEREOF

(71) Applicant: DIC Corporation, Tokyo (JP)

(72) Inventors: Yasuyo Yoshimoto, Sakura (JP);
Kunihiro Morinaga, Ichihara (JP);
Hiroshi Kinoshita, Sakura (JP);
Masamichi Hayashi, Sakura (JP)

(73) Assignee: DIC Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/647,386

(22) Filed: Jul. 12, 2017

(65) Prior Publication Data

US 2018/0002261 A1 Jan. 4, 2018

Related U.S. Application Data

(62) Division of application No. 14/431,968, filed as application No. PCT/JP2013/075649 on Sep. 24, 2013, now Pat. No. 9,738,580.

(30) Foreign Application Priority Data

Sep. 28, 2012 (JP) .................................. 2012-216516
Nov. 29, 2012 (JP) .................................. 2012-261035

(51) Int. Cl.
*C07C 37/11* (2006.01)
*C08L 63/00* (2006.01)
(Continued)

(52) U.S. Cl.
CPC ............ *C07C 37/11* (2013.01); *C07D 301/28* (2013.01); *C07D 303/27* (2013.01); *C08L 63/00* (2013.01); *C08L 2201/02* (2013.01)

(58) Field of Classification Search
CPC ..... C07D 301/28; C07D 303/27; C08L 63/00; C08L 2201/02; C07C 37/11
(Continued)

(56) References Cited

U.S. PATENT DOCUMENTS 5,302,672 A 4/1994 Ogura et al.
6,037,426 A 3/2000 Shimizu et al.
(Continued)

FOREIGN PATENT DOCUMENTS

CN 104684902 A 6/2015
EP 1184419 A2 3/2002
(Continued)

OTHER PUBLICATIONS

Kotake et al., JP 2010-106150 A machine translation in English, May 13, 2010 (Year: 2010).*

(Continued)

*Primary Examiner* — David T Karst
(74) *Attorney, Agent, or Firm* — Locke Lord LLP; James E. Armstrong, IV; Nicholas J. DiCeglie, Jr.

(57) ABSTRACT

The present invention provides an epoxy compound which is 2,2',7,7'-tetraglycidyloxy-1,1'-binaphthalene. Also, the present invention provides a method for producing [1,1'-binaphthalene]-2,2',7,7'-tetraol, the method including a step of bringing a crude product produced by dimerization reaction of naphthalene-2,7-diol or a naphthalene-2,7-diol derivative into contact with an aromatic solvent; a step of separating [1,1'-binaphthalene]-2,2',7,7'-tetraol dissolved in the aromatic solvent from insoluble substances; and a step of removing the solvent from a solution of [1,1'-binaphtha-
(Continued)

lene]-2,2',7,7'-tetraol. The present invention also provides a method for producing an epoxy compound, the method including reacting [1,1'-binaphthalene]-2,2',7,7'-tetraol or [1,1'-binaphthalene]-2,2',7,7'-tetraol monohydrate with epihalohydrin.

4 Claims, 7 Drawing Sheets

(51) Int. Cl.
  *C07D 301/28* (2006.01)
  *C07D 303/27* (2006.01)
  *C07C 39/14* (2006.01)
(58) Field of Classification Search
  USPC .......................................................... 525/523
  See application file for complete search history.

(56) References Cited

U.S. PATENT DOCUMENTS

| | | | |
|---|---|---|---|
| 2011/0124775 A1 | 5/2011 | Wada | |
| 2015/0353456 A1 | 12/2015 | Yoshimoto et al. | |

FOREIGN PATENT DOCUMENTS

| | | | |
|---|---|---|---|
| JP | 59-098027 | A | 6/1984 |
| JP | 61-178974 | A | 8/1986 |
| JP | 01-168633 | A | 7/1989 |
| JP | 04-217675 | A | 8/1992 |
| JP | 04-337314 | A | 11/1992 |
| JP | 06-184131 | A | 7/1994 |
| JP | 08-245459 | A | 9/1996 |
| JP | 2001-39913 | A | 2/2001 |
| JP | 3137202 | B | 2/2001 |
| JP | 2001-089644 | A | 4/2001 |
| JP | 2004-111380 | A | 4/2004 |
| JP | 2007-308640 | A | 11/2007 |
| JP | 2010-024417 | A | 2/2010 |
| JP | 2010-106150 | A | 5/2010 |
| JP | 2011-037941 | A | 2/2011 |
| TW | 575631 | B | 2/2004 |
| WO | WO-2014050789 | A1 | 4/2014 |

OTHER PUBLICATIONS

Matsushita, M et al., "Heterogeneously Catalyzed Aerobic Oxidative Biaryl Coupling of 2-Naphthols and Substituted Phenols in Water," Journal of American Chemical Society, 2005, vol. 127, No. 18, pp. 6632-6640.

Kurt, B. et al., "Uber das 2,7,2',7'-Tetraoxy-dinaphthyl-(1.1')", Chemische Berichte, 1937, vol. 70, p. 1341-1348.
Sakamoto, T. et al., "Catalytic Activities of $CuSO_4/Al_2O_3$ in Dehydrogenation of Arenes by Dioxygen," Journal of Organic Chemisty, 1997, vol. 62, No. 10, pp. 3194-3199.
International Search Report dated Nov. 19, 2013, issued for PCT/JP2013/075649.
Shun-jun Ji, "Microwave -assisted efficent oxidative coupling of 2-naphthols in the solid state," Synthetic Communications, 2002, vol. 32. No. 19, pp. 3069-3074.
Notification of the First Office Action, issued in corresponding Chinese Patent Application No. CN 201380050884.5, dated Nov. 3, 2015.
Notification of Reasons for Refusal, issued in corresponding Japanese Patent Application No. JP 2014-538480, dated Dec. 17, 2014.
Notification of Reasons for Refusal, issued in corresponding Korean Patent Application No. KR 10-2015-7006104, dated May 16, 2016.
Uchida et al., JP 2007-308640 A machine translation in English, Nov. 29, 2007.
Akiyama et al., JP 08-245459 A machine translation in English, Sep. 24, 1996.
Kobayashi et al., JP 2011-037941 A machine translation in English, Feb. 24, 2011.
International Search Report dated May 27, 2014, issued for PCT/JP2014/055463.
Zhang Yu Dragon et al., "Practical Ceramic Materials Manual 1st edition," Chemical Industry Publishers, Materials Science and Process Publishing Center, Jul. 2006, pp. 364-366 and English comment is included.
Office Action dated May 31, 2016, issued for the Chinese patent application No. 201480025275.9 and English translation thereof.
Office Action dated Feb. 15, 2017, issued for the Chinese patent application No. 201480025275.9 and English translation thereof.
European Search Report and European Search Opinion dated Oct. 17, 2017, issued for the European patent application No. 17 171 997.4.
European Search Report and European Search Opinion dated Oct. 11, 2016, issued for the European patent application No. 14 760 547.1.
Office Action dated Jan. 22, 2015, issued for the Japanese patent application No. 2014-056368 and English translation thereof.
Office Action dated Dec. 3, 2015, issued for the Japanese patent application No. 2014-040373 and English translation thereof.
Office Action dated Jul. 5, 2016, issued for the Korean patent application No. 10-2015-7027444 and English translation thereof.
Office Action dated Jun. 20, 2017, issued for the Taiwanese patent application No. 103107558 and partial machine English translation thereof.
Handbook of Fillers, 3d edition, Table Data: Physical and Chemical Properties (2010).

\* cited by examiner

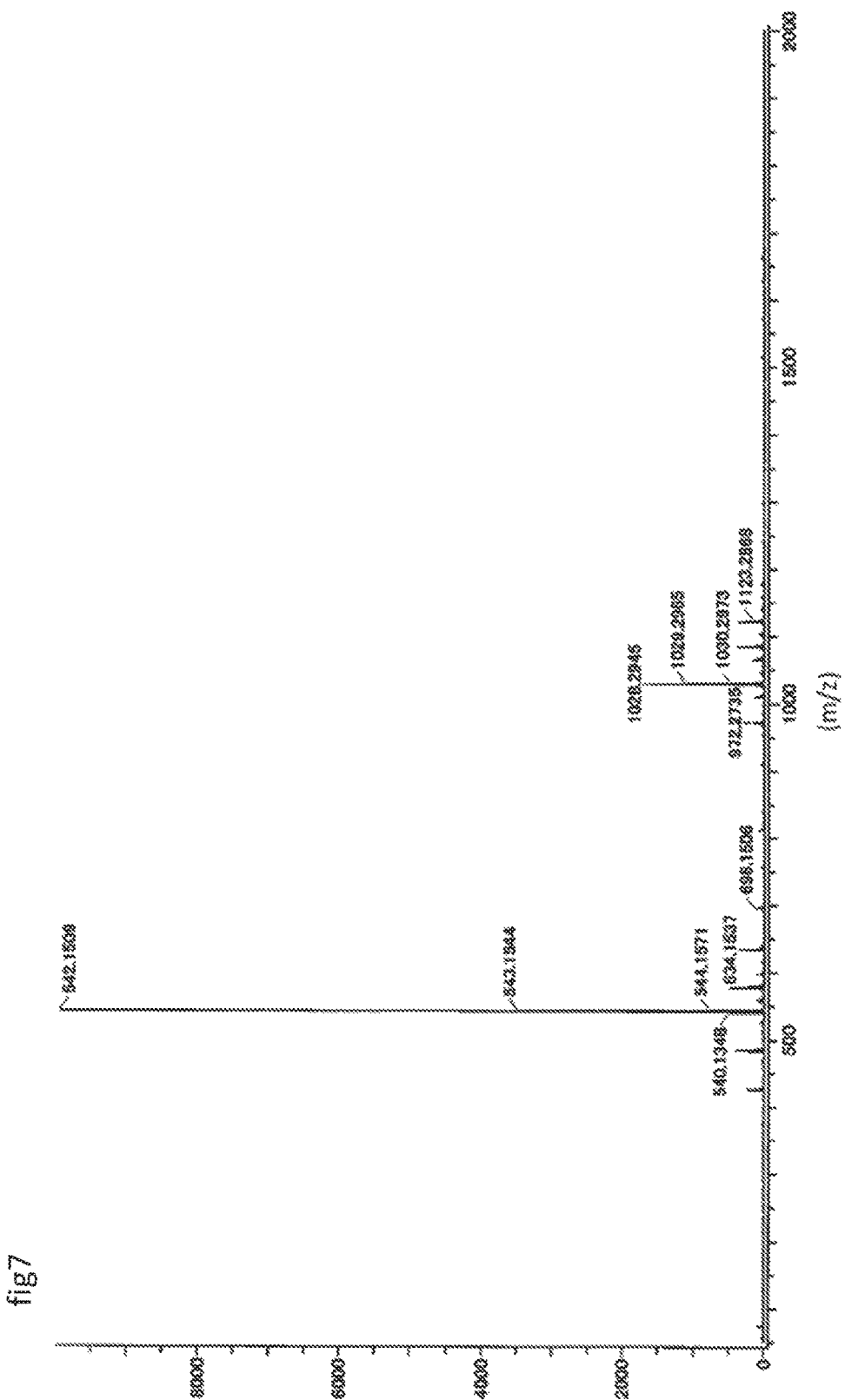

EPOXY COMPOUND, METHOD FOR PRODUCING THE SAME, EPOXY RESIN COMPOSITION, AND CURED PRODUCT THEREOF

This application is a divisional application of U.S. Ser. No. 14/431,968 filed on Mar. 27, 2015, which claims the right of priority under 35 U.S.C. § 119 based on Japanese Patent Application Nos. 2012-261035 filed on Nov. 29, 2012 and 2012-216516 filed on Sep. 28, 2012. The entire contents of these applications are incorporated herein by reference in their entirety.

TECHNICAL FIELD

The present invention relates to an epoxy compound and a method for producing the compound which provides an epoxy resin composition having good solvent solubility and excellent heat resistance and moisture absorption resistance.

BACKGROUND ART

Epoxy resin compositions each containing an epoxy compound and a curing agent for the epoxy compound are widely used in laminated-plate resin materials, electric insulating materials, semiconductor encapsulating materials, fiber-reinforced composite materials, coating materials, molding materials, adhesive materials, etc. in view of the excellent physical properties such as heat resistance, moisture absorption resistance, and the like.

In recent years, in these various applications, particularly in the field of advanced materials, performance characterized by heat resistance, moisture absorption resistance, and low coefficient of thermal expansion property has been required to be further improved. Further, according to regulations to environmental problems and the like, high-melting-point solders not using lead (lead-free solders) have become mainstream, and the working temperatures of the lead-free solders are about 20° C. to 40° C. higher than usual eutectic solders, thereby requiring epoxy resin cured products to have higher heat resistance and higher moisture absorption resistance than ever.

Examples of known epoxy resin materials which can comply with the requirements for high degrees of heat resistance and moisture absorption resistance and low coefficient of thermal expansion property include tetrafunctional naphthalene-based epoxy compounds represented by a structural formula below (Patent Literature 1).

[Chem. 1]

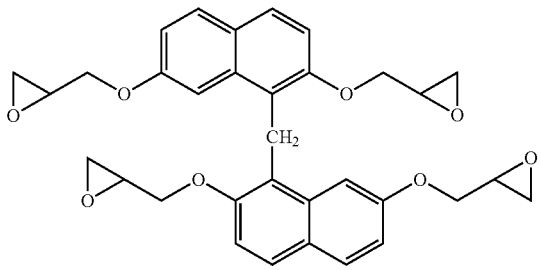

In comparison with general phenol novolac-type epoxy compounds, the tetrafunctional naphthalene-based epoxy compounds have a naphthalene skeleton having high heat resistance and high hydrophobicity, a high crosslink density due to tetrafunctionality, and a molecular structure with excellent symmetry, and thus cured products thereof exhibit very excellent heat resistance, moisture absorption resistance, and low coefficient of thermal expansion property. However, higher performance has recently been required for resistance, and further improvement has been required. Further, since the tetrafunctional naphthalene-based epoxy compounds have low solubility in solvents, the characteristics of the cured products have been not sufficiently exhibited in, for example, manufacture of printed circuit boards.

It is considered to be effective as a method for improving heat resistance that in the tetrafunctional naphthalene-based epoxy compounds, naphthalene rings are directly bonded to each other, not bonded through a methylene structure. There is described an epoxy compound having a bi(dihydroxynaphthalene) structure in which a dihydroxynaphthalene dimer has a direct single bond without containing a methylene structure (Patent Literatures 2 to 5). The positions of hydroxyl groups in dihydroxynaphthalene and the bond position in a dimer are important factors which influence the physical properties of an epoxy resin using the compound, such as the softening point, solvent solubility, the heat resistance of cured products thereof, and the like. However, any one of Patent Literatures 2 to 5 does not specify the positions of hydroxyl groups in dihydroxynaphthalene and the bond position in a dimer, and does not specifically describe the compound.

Synthesis of [1,1'-binaphthalene]-2,2',7,7'-tetraol generally uses coupling reaction of dihydroxynaphthalene or a dihydroxynaphthalene derivative. This reaction is selective coupling reaction at the 1,1'-positions of 2,7-dihydroxynaphthalene, and thus [1,1'-binaphthalene]-2,2',7,7'-tetraol with high purity can be produced, thereby producing an epoxy compound exhibiting excellent performance such as a low softening point, low melt viscosity, high solvent solubility, and the like. Also, an epoxy compound produced from [1,1'-binaphthalene]-2,2',7,7'-tetraol of the present invention was not synthesized in the past and is thus a novel epoxy compound.

[1,1'-Binaphthalene]-2,2',7,7'-tetraol has a molecular structure very similar to that of 1,1-bis(2,7-dihydroxy-1-naphthyl)alkane described in Patent Literature 6, but has excellent heat resistance and handleability at a low temperature because it does not have an alkylene group, which is unstable under high-temperature conditions, and has a lower melting point than 1,1-bis(2,7-dihydroxy-1-naphthyl)alkane. Also, [1,1'-binaphthalene]-2,2',7,7'-tetraol can take the forms of an anhydride and hydrates such as monohydrate and dehydrate. The anhydride has a melting point of 218° C., while the monohydrate has a softening point of 124° C. as well as a melting point and thus application in a lower temperature region can be expanded.

Non-Patent Literatures 1 to 3 describe examples of synthesis of [1,1'-binaphthalene]-2,2',7,7'-tetraol. The products of oxidative coupling reaction of naphthalene-2,7-diol include [1,1'-binaphthalene]-2,2',7,7'-tetraol, unreacted raw materials, and multimers such as a trimer, a tetramer, and the like, which have similar dissolution behaviors in a solvent due to similar structures and thus cannot be easily separated from each other. Therefore, recrystallization with carbon disulfide, benzene, and ethanol described in the literatures produces mixed crystals of [1,1'-binaphthalene]-2,2',7,7'-tetraol and impurities, and [1,1'-binaphthalene]-2,2',7,7'-tetraol with high purity cannot be produced. This is a cause for failing to obtain expected values of physical properties, such as high heat resistance and moisture resistance, of resins obtained by using the compound.

CITATION LIST

Patent Literature

PTL 1: Japanese Patent No. 3137202
PTL 2: Japanese Unexamined Patent Application Publication No. 2004-111380
PTL 3: Japanese Unexamined Patent Application Publication No. 2007-308640
PTL 4: Japanese Unexamined Patent Application Publication No. 2010-24417
PTL 5: Japanese Unexamined Patent Application Publication No. 2010-106150
PTL 6: Japanese Unexamined Patent Application Publication No. 4-217675

Non-Patent Literature

NPL 1: Chemische Berichte, 70 (1937), 1341-1348
NPL 2: Chinese Chemical Letters, 20 (2009), 663-667
NPL 3: Journal of American Chemical Society, 127 (2005), 6632-6640

SUMMARY OF INVENTION

Technical Problem

A problem to be solved by the present invention is to provide an epoxy resin composition which has solvent solubility, a low softening point, and easy moldability due to low melt viscosity and which realizes a cured product having good heat resistance and excellent moldability and dimensional stability after molding because the resultant cured product exhibits excellent moisture absorption resistance and low coefficient of thermal expansion property, and also provide a cured product of the composition and a novel epoxy compound giving these performances.

Also, a problem to be solved by the present invention is to provide a method for producing high-purity [1,1'-binaphthalene]-2,2',7,7'-tetraol and a [1,1'-binaphthalene]-2,2',7,7'-tetraol monohydrate.

Solution to Problem

As a result of earnest research, the inventors found that the above problems can be solved by using an epoxy compound, that is, 2,2',7,7'-tetraglycidyloxy-1,1'-binaphthalene, which is produced by reaction of [1,1'-binaphthalene]-2,2',7,7'-tetraol with epihalohydrin, the [1,1'-binaphthalene]-2,2',7,7'-tetraol being produced by selective coupling reaction at the 1,1'-positions of 2,7-dihydroxynaphthalene, leading to the achievement of the present invention.

That is, the present invention relates to 2,2',7,7'-tetraglycidyloxy-1,1'-binaphthalene, a method for producing an epoxy compound by reacting [1,1'-binaphthalene]-2,2',7,7'-tetraol with epihalohydrin, an epoxy resin composition containing 2,2',7,7'-tetraglycidyloxy-1,1'-binaphthalene and a curing agent, and a cured product obtained by curing reaction of the epoxy resin composition.

Also, the present invention provides a method for producing [1,1'-binaphthalene]-2,2',7,7'-tetraol, the method including:

a step of bringing a crude product into contact with an aromatic solvent, the crude product being produced by dimerization reaction of naphthalene-2,7-diol or a naphthalene-2,7-diol derivative;

a step of separating [1,1'-binaphthalene]-2,2',7,7'-tetraol dissolved in the aromatic solvent from impurities; and a step of removing the solvent from a solution of [1,1'-binaphthalene]-2,2',7,7'-tetraol.

Further, the present invention provides a method for producing [1,1'-binaphthalene]-2,2',7,7'-tetraol, the method including:

a step of bringing a crude product into contact with an aromatic solvent, the crude product being produced by dimerization reaction of naphthalene-2,7-diol or a naphthalene-2,7-diol derivative;

a step of separating the [1,1'-binaphthalene]-2,2',7,7'-tetraol dissolved in the aromatic solvent from impurities; and a step of heat-concentrating the resultant solution of [1,1'-binaphthalene]-2,2',7,7'-tetraol to produce [1,1'-binaphthalene]-2,2',7,7'-tetraol.

Further, the present invention provides a method for producing a [1,1'-binaphthalene]-2,2',7,7'-tetraol monohydrate, the method including a step of reacting the resultant [1,1'-binaphthalene]-2,2',7,7'-tetraol with water to produce a [1,1'-binaphthalene]-2,2',7,7'-tetraol monohydrate.

Advantageous Effects of Invention

According to the present invention, the resultant epoxy compound has a low softening point, low melt viscosity, and good solvent solubility, and an epoxy resin composition containing the epoxy compound can provide an epoxy resin cured product having excellent performance for heat resistance and moisture absorption resistance.

Also, a method for producing [1,1'-binaphthalene]-2,2',7,7'-tetraol of the present invention can produce [1,1'-binaphthalene]-2,2',7,7'-tetraol with high purity. In addition, [1,1'-binaphthalene]-2,2',7,7'-tetraol monohydrate with high purity can be produced by bringing water into contact with the resultant [1,1'-binaphthalene]-2,2',7,7'-tetraol.

BRIEF DESCRIPTION OF DRAWINGS

FIG. 7 is a MS spectrum of Example 6.

DESCRIPTION OF EMBODIMENTS

Figure 1:
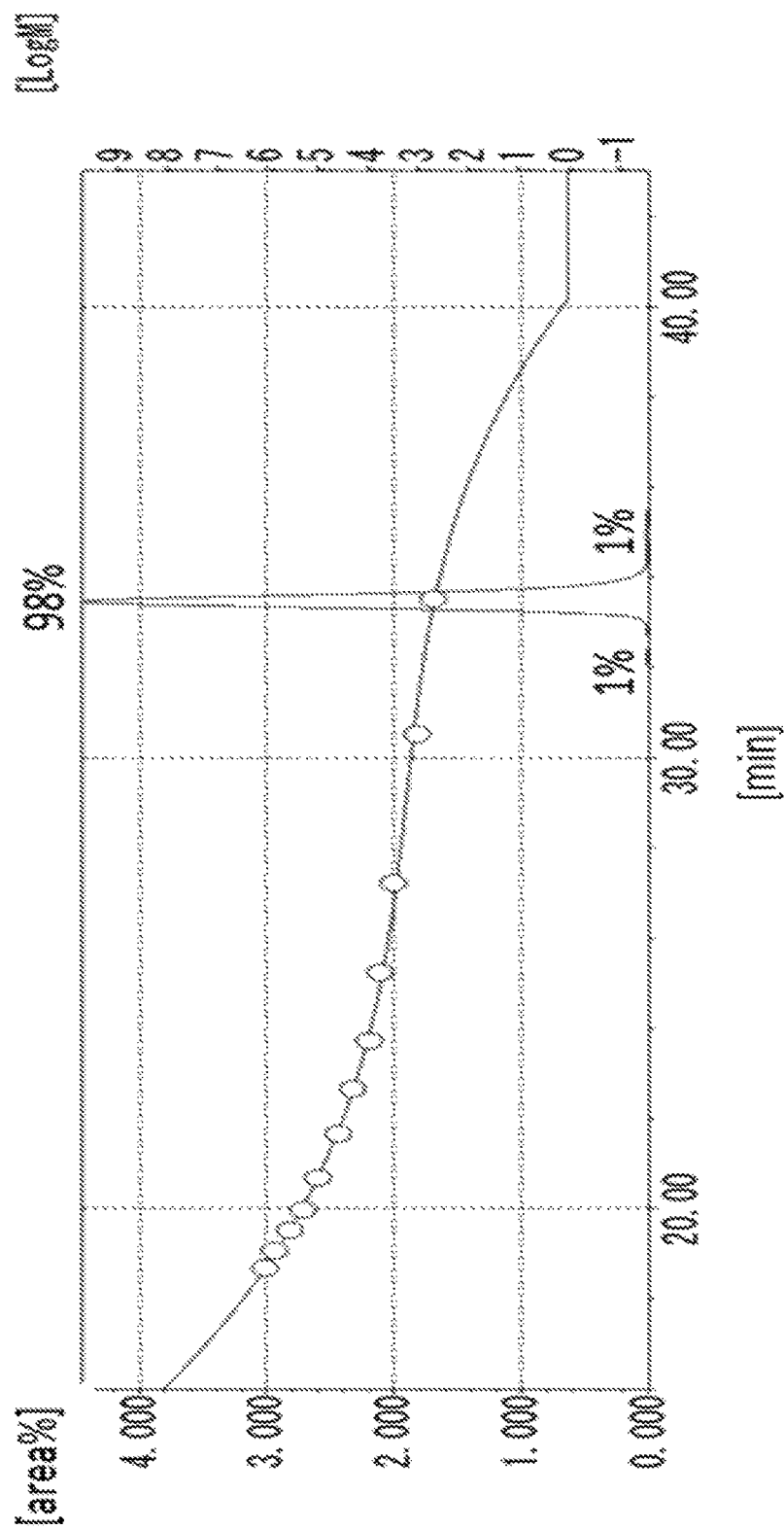
FIG. 1 is a GPC chart of [1,1'-binaphthalene]-2,2',7,7'-tetraol produced in Example 1.

The present invention is described in detail below.

[Epoxy Compound]

An epoxy compound of the present invention can be produced by, for example, a production method of the present invention in which [1,1'-binaphthalene]-2,2',7,7'-tetraol is reacted with epihalohydrin, and is specifically represented by a structural formula (1) below.

[Chem. 2]

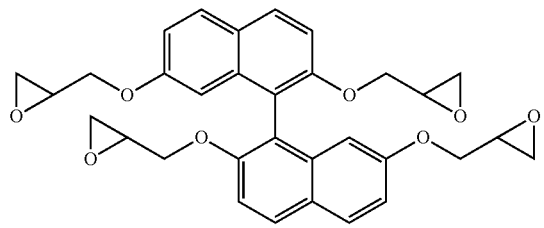

(1)

[1,1'-Binaphthalene]-2,2',7,7'-tetraol which is a raw material of the epoxy compound of the present invention can be produced by coupling reaction of dihydroxynaphthalene or a dihydroxynaphthalene derivative. In the coupling reaction of dihydroxynaphthalene or a dihydroxynaphthalene derivative, a multimer cannot be easily produced because of selective coupling reaction of 2,7-dihydroxynaphthalene at the 1,1'-positions, and the resultant [1,1'-binaphthalene]-2,2',7,7'-tetraol has a lower melting point than 1,1'-methylenebis(2,7-dihydroxynaphthalene) having a similar structure. In addition, a diglycidyl ether thereof has a lower softening point, lower viscosity, and higher solvent solubility than a tetrafunctional diglycidyl ether of 1,1'-methylenebis(2,7-dihydroxynaphthalene).

The method for producing an epoxy compound of the present invention is described in detail below, but the method for producing an epoxy compound of the present invention is not limited to this.

That is, the production method of the present invention includes reaction of [1,1'-binaphthalene]-2,2',7,7'-tetraol with epihalohydrin. A specific example of the method includes adding epihalohydrin at a ratio of 2 to 10 times (molar basis) the number of moles of phenolic hydroxyl groups in a phenol compound, and performing reaction at a temperature of 20° C. to 120° C. for 0.5 to 10 hours while further adding at a time or gradually a basic catalyst at a ratio (molar basis) of 0.9 to 2.0 times the number of moles of the phenolic hydroxyl groups. The basic catalyst used may be a solid or an aqueous solution thereof, and when the aqueous solution is used, the method may be performed by continuously adding the catalyst, continuously distilling off water and epihalohydrin from the reaction mixture under reduced pressure or atmospheric pressure, and further removing water by liquid separation and continuously returning epihalohydrin to the reaction mixture.

In industrial production, new epihalohydrin is used in preparation of a first batch for producing an epoxy compound, but in a second batch or later, epihalohydrin recovered from crude reaction products can be combined with new epihalohydrin corresponding to a loss due to the consumption by the reaction, thereby causing an economical advantage. In this case, the epihalohydrin used is not particularly limited, and examples thereof include epichlorohydrin, epibromohydrin, β-methylepichlorohydrin, and the like. In view of industrially easy availability, epichlorohydrin is particularly preferred.

Specific examples of the basic catalyst include alkaline-earth metal hydroxides, alkali metal carbonates, alkali metal hydroxides, and the like. In view of excellent catalyst activity in epoxy resin synthesis reaction, alkali metal hydroxides are particularly preferred, and examples thereof include sodium hydroxide, potassium hydroxide, and the like. When used, the basic catalyst may be used in the form of an aqueous solution of about 10% to 55% by mass or may be used in a solid form. In addition, the reaction rate of synthesis of an epoxy compound can be increased by combining an organic solvent. Examples of the organic solvent include, but are not particularly limited to, ketones such as acetone, methyl ethyl ketone, and the like; alcohols such as methanol, ethanol, 1-propylalcohol, isopropylalcohol, 1-butanol, secondary butanol, tertiary butanol, and the like; cellosolves such as methyl cellosolve, ethyl cellosolve, and the like; ethers such as tetrahydrofuran, 1,4-dioxane, 1,3-dioxane, diethoxyethane, and the like; and aprotic polar solvents such as acetonitrile, dimethylsulfoxide, dimethylformamide, and the like. These organic solvents may be used alone or in appropriate combination of two or more in order to adjust polarity.

The product of the epoxidation reaction is washed with water and then unreacted epihalohydrin and the organic solvent combined are distilled off by distillation under heating and reduced pressure. Further, in order to produce an epoxy resin containing little hydrolyzable halogen, the resultant epoxy resin can be dissolved again in an organic solvent such as toluene, methyl isobutyl ketone, methyl ethyl ketone, or the like, and an aqueous solution of an alkali meta hydroxide such as sodium hydroxide, potassium hydroxide, or the like can be added to the resultant solution and subjected to further reaction. In this case, a phase transfer catalyst such as a quaternary ammonium salt, crown ether, or the like may be present for the purpose of improving the reaction rate. When the phase transfer catalyst is used, the amount of use is preferably a ratio of 0.1 to 3.0 parts by mass relative to 100 parts by mass of the epoxy resin used. After the finish of the reaction, the produced salt is removed by filtration and washing with water, and further the solvent such as toluene, methyl isobutyl ketone, or the like is removed by distillation under heating and reduced pressure, whereby a target novel epoxy compound of the present invention can be produced.

[Tetraol]

Although [1,1'-binaphthalene]-2,2',7,7'-tetraol which is a raw material of the epoxy compound of the present invention may be produced by a known common method, the method for producing [1,1'-binaphthalene]-2,2',7,7'-tetraol of the present invention is characterized by a purification step of dissolving a crude product produced by dimerization reaction of naphthalene-2,7-diol or a naphthalene-2,7-diol derivative in an aromatic solvent and then separating [1,1'-binaphthalene]-2,2',7,7'-tetraol dissolved in the aromatic solvent from insoluble substances, and is thus characterized by being capable of producing [1,1'-binaphthalene]-2,2',7,7'-tetraol with high purity.

Specifically, the purification step includes bringing the crude product produced by dimerization reaction of naphthalene-2,7-diol or a naphthalene-2,7-diol derivative and containing [1,1'-binaphthalene]-2,2',7,7'-tetraol as a main component into contact with the aromatic solvent, dissolving [1,1'-binaphthalene]-2,2',7,7'-tetraol by reflux, precipitating dissolved impurities by cooling to room temperature, separating a solution of [1,1'-binaphthalene]-2,2',7,7'-tetraol from insoluble impurities, and then removing the solvent from the solution of [1,1'-binaphthalene]-2,2',7,7'-tetraol to produce [1,1'-binaphthalene]-2,2',7,7'-tetraol.

The product produced by dimerization reaction of naphthalene-2,7-diol or a naphthalene-2,7-diol derivative includes [1,1'-binaphthalene]-2,2',7,7'-tetraol and also includes the unreacted raw material, a trimer, a tetramer, and the like, which are all compounds having similar structures and exhibiting very similar properties such as crystallinity and solvent solubility, and thus cannot be easily separated from each other by using a recrystallization method, a reprecipitation method, or the like. However, these compounds have low solubility in the aromatic solvent, and thus only [1,1'-binaphthalene]-2,2',7,7'-tetraol can be separated as a dissolved substance or a precipitate by using a slight difference in solubility between [1,1'-binaphthalene]-2,2',7,7'-tetraol and other by-products.

The solubility in the aromatic solvent decreases as the molecular weight increases in the order of naphthalene-2,7-diol or a naphthalene-2,7-diol derivative which is the raw material, [1,1'-binaphthalene]-2,2',7,7'-tetraol, a trimer, and a tetramer, and a pentamer or higher multimer becomes insoluble.

Examples of the aromatic solvent include benzene; alkylbenzene such as toluene, xylene, ethylbenzene, cumene, and the like; and alkoxybenzene such as anisole, phenetol, and the like, and toluene or xylene is preferred. The aromatic solvents are preferably used alone or as a mixture of two or more as the solvent, and an alcohol solvent, a ketone solvent, an ester solvent, and the like may be mixed within a range in which the effect of the present invention is not impaired.

The amount of the aromatic solvent used falls in an appropriate range determined by purity and yield, and when purity is regarded as important, a smaller amount of the solvent is used, and when yield is regarded as important, a larger amount of the solvent is used. With an excessively small amount out of the appropriate range, [1,1'-binaphthalene]-2,2',7,7'-tetraol precipitates, while with an excessively large amount, impurities having lower solubility than [1,1'-binaphthalene]-2,2',7,7'-tetraol are dissolved, and thus desired [1,1'-binaphthalene]-2,2',7,7'-tetraol cannot be produced. Therefore, the amount of the aromatic solvent used is preferably 50 to 150 mL and more preferably 80 to 100 mL relative to 1 g of [1,1'-binaphthalene]-2,2',7,7'-tetraol.

The method for separating [1,1'-binaphthalene]-2,2',7,7'-tetraol dissolved in the aromatic solvent from insoluble substances in the purification step is not particularly limited, and a filtration method or a centrifugal separation method can be used.

[1,1'-Binaphthalene]-2,2',7,7'-tetraol can be obtained by removing the solvent from the resultant solution of [1,1'-binaphthalene]-2,2',7,7'-tetraol according to a known common method. The method for removing the solvent is not particularly limited, and a method such as vacuum drying, heat drying, spray drying, or the like can be used.

Next, the method for producing [1,1'-binaphthalene]-2,2',7,7'-tetraol is characterized by a purification step of dissolving the crude product produced by dimerization reaction of naphthalene-2,7-diol or a naphthalene-2,7-diol derivative in an aromatic solvent, separating [1,1'-binaphthalene]-2,2',7,7'-tetraol dissolved in the aromatic solvent from insoluble substances, and then heat-concentrating the resultant solution to precipitate a solid of [1,1'-binaphthalene]-2,2',7,7'-tetraol. This method can preferably produce [1,1'-binaphthalene]-2,2',7,7'-tetraol with higher purity.

Specifically, the purification step includes preparing an aromatic solvent mixture of the crude product which is produced by dimerization reaction of naphthalene-2,7-diol or a naphthalene-2,7-diol derivative and which contains [1,1'-binaphthalene]-2,2',7,7'-tetraol as a main component, dissolving [1,1'-binaphthalene]-2,2',7,7'-tetraol by reflux, precipitating slightly dissolved impurities by cooling to room temperature, separating the impurities insoluble in the solvent, removing the solvent from the resultant solution under heating and stirring until a solid of [1,1'-binaphthalene]-2,2',7,7'-tetraol is sufficiently precipitated, and then performing hot-filtration while keeping a high temperature.

In the purification step, when only the step of separating [1,1'-binaphthalene]-2,2',7,7'-tetraol dissolved in the aromatic solvent from insoluble substances is performed, there remain naphthalene-2,7-diol or a naphthalene-2,7-diol derivative used as the raw material and easily dissolved in the aromatic organic solvent and trace amounts of by-products such as a multimer or the like. Therefore, the purification step is effective when further purification is required, such as when higher purity is required or when the unreacted raw material is present.

In the purification step, in the step of precipitating a solid of [1,1'-binaphthalene]-2,2',7,7'-tetraol by heat-concentrating the solution obtained by removing insoluble substances, only [1,1'-binaphthalene]-2,2',7,7'-tetraol preset in a large amount can be precipitated leaving small amounts of impurities dissolved, and [1,1'-binaphthalene]-2,2',7,7'-tetraol with high purity can be produced. The purity is higher than in the case using a method other than heat concentration, that is, in the case using low-temperature concentration, reprecipitation, or recrystallization.

In the purification step, the method for separating [1,1'-binaphthalene]-2,2',7,7'-tetraol dissolved in the aromatic solvent from insoluble substances is not particularly limited, and a filtration method, a centrifugal separation method, or the like can be used. In the filtration method, filtration is preferably performed under high-temperature conditions because precipitation of impurities can be prevented. The temperature of the mixture and a filter is 60° C. or more, preferably 80° C. or more, and more preferably 100° C. or more, and the upper limit is the boiling point of the aromatic solvent.

The aromatic solvent remaining in a small amount in [1,1'-binaphthalene]-2,2',7,7'-tetraol produced by heat concentration may be removed by vacuum drying or heat drying.

Next, [1,1'-binaphthalene]-2,2',7,7'-tetraol produced by the method described above is brought into contact with water, and consequently [1,1'-binaphthalene]-2,2',7,7'-tetraol monohydrate with high purity can be produced.

The method for bringing [1,1'-binaphthalene]-2,2',7,7'-tetraol into contact with water is not particularly limited as long as it is a method capable of thoroughly bringing [1,1'-binaphthalene]-2,2',7,7'-tetraol into contact with water. Specifically, [1,1'-binaphthalene]-2,2',7,7'-tetraol may be stirred in water or water may be sprayed on a powder of [1,1'-binaphthalene]-2,2',7,7'-tetraol.

The contact product between [1,1'-binaphthalene]-2,2',7,7'-tetraol and water is preferably dried at atmospheric pressure. The drying temperature is preferably in a range of 40° C. to 130° C. and particularly preferably 80° C. to 100° C. The drying time varies with the water content, and drying at 80° C. may be performed for about 10 days and drying at 100° C. may be performed for about 20 hours.

The method for producing [1,1'-binaphthalene]-2,2',7,7'-tetraol of the present invention characterized by the step of separating [1,1'-binaphthalene]-2,2',7,7'-tetraol dissolved in the aromatic solvent from insoluble substances or the step of separating [1,1'-binaphthalene]-2,2',7,7'-tetraol dissolved in the aromatic solvent from insoluble substances and then heat-concentrating the resultant solution to precipitate a solid of [1,1'-binaphthalene]-2,2',7,7'-tetraol is suitable for purifying crude products of various reactions of dimerization of naphthalene-2,7-diol or a naphthalene-2,7-diol derivative. Examples of the reactions include homocoupling reaction of naphthalene-2,7-diol or a halide, a silane derivative, a tin derivative, a lithium derivative, a boronic acid derivative, or a sulfonic acid derivative such as trifluoromethanesulfonic acid or the like of naphthalene-2,7-diol; coupling reaction of a combination of any two of naphthalene-2,7-diol and a halide, a silane derivative, a tin derivative, a lithium derivative, a boronic acid derivative, a sulfonic acid derivative such as trifluoromethanesulfonic acid or the like, an alkoxy derivative, a magnesium halide derivative, a zinc halide derivative, and the like of naphthalene-2,7-diol; and the like. The production method of present invention is particularly suitable for purifying a crude product produced by oxidative coupling reaction of naphthalene-2,7-diol or a halide, which is capable of easily dimerizing naphthalene-2,7-diol without derivatization.

Examples of a reaction catalyst used in the oxidative coupling reaction of naphthalene-2,7-diol include chlorides, bromides, hydroxides, sulfates, nitrates, hydrogensulfates, acetates, and oxides of metals such as iron, copper, silver, nickel, magnesium, cobalt, manganese, titanium, ruthenium, palladium, rhodium, and the like; double salts such as iron ammonium sulfate, copper hydrogen chloride, and the like; copper salt-amine complex salts such as copper chloride-tetramethylethylenediamine complex and the like; the metal salts supported on silica, alumina, titanium oxide, or the like; peroxides such as di-tert-butyl peroxide and the like; (NO)-ruthenium salen complexes; oxovanadium complexes; and the like. These can be used alone or in combination.

The oxidative coupling reaction of naphthalene-2,7-diol described above can be performed without using a solvent or in a solvent. When the reaction is performed in a solvent, according to the catalyst, the solvent can be selected from water; alcohol organic solvents such as methanol, ethanol, and the like; ester organic solvents such as ethyl acetate, propyl acetate, and the like; halogen-based organic solvents such as dichloromethane, 1,2-dichlorethane, and the like; aromatic organic solvents such as benzene, toluene, chlorobenzene, and the like; ketone organic solvents such as acetone, 2-butanone, and the like; nitrile organic solvents such as acetonitrile, propionitrile, and the like; ether organic solvents such as diethyl ether, tetrahydrofuran, 1,4-dioxane, and the like; amide organic solvents such as N,N-dimethylformamide, N,N-dimethylacetamide, N-methyl-2-purrolydone, and the like; dimethyl sulfoxide; and the like; and combinations thereof.

The oxidative coupling reaction of naphthalene-2,7-diol described above is specifically described below with reference to reaction using ferric chloride hexahydrate as the catalyst as an example.

The reaction using ferric chloride hexahydrate as the catalyst includes reaction of naphthalene-2,7-diol with the ferric chloride hexahydrate in a mixed solvent of water and a hydrophilic organic solvent, thereby synthesizing [1.1'-binaphthalene]-2,2',7,7'-tetraol.

In the reaction, the amount of the ferric chloride hexahydrate is not particularly limited as long as the molar ratio thereof relative to naphthalene-2,7-diol as a starting material is equal to or higher than a theoretically required amount of 0.5. However, even with a large amount, reactivity is not changed, and thus the amount of use is preferably within a range of 1.0 to 2.0.

The reaction may be performed in a single water solvent, but a hydrophilic organic solvent is preferably added for swelling and dispersing aggregates of water insoluble products and facilitating stirring because the aggregates of water-insoluble products form lumps. The mixing ratio between water and the hydrophilic organic solvent in a mixed solvent is not particularly limited, but water and the hydrophilic organic solvent are preferably mixed at a weight ratio of water/hydrophilic organic solvent within a range of 99/1 to 90/10.

The hydrophilic organic solvent is not particularly limited as long as it has compatibility with water and can dissolve the product. Examples of the solvent include alcohol organic solvents such as methanol, ethanol, 1-propanol, 2-propanl, and the like; ketone organic solvents such as acetone, 2-butanone, and the like; nitrile organic solvents such as acetonitrile, propionitrile, and the like; ether organic solvents such as diethyl ether, tetrahydrofuran, 1,4-dioxane, and the like; amide organic solvents such as N,N-dimethylformamide, N,N-dimethylacetamide, N-methyl-2-pyrrolidone, and the like; dimethyl sulfoxide; and mixed solvents thereof. Preferred examples of the hydrophilic organic solvent include alcohol organic solvents, and methanol, ethanol, and 2-propanol are more preferred.

In the reaction, the method for charging naphthalene-2,7-diol, the ferric chloride hexahydrate, water, and the hydrophilic organic solvent is not particularly limited, but a preferred method is 1) a method of adding 2,7-dihydroxynaphthalene in the form of a powder, a solution in a hydrophilic polar solvent, or a mixed solution in water and the hydrophilic polar solvent to a reactor in which a mixed solution of the ferric chloride hexahydrate in water or water and the hydrophilic polar solvent is mixed and stirred, or 1) a method of adding the ferric chloride hexahydrate as an aqueous solution or a mixed solution in water and the hydrophilic polar solvent to a reactor in which 2,7-dihydroxynaphthalene in the form of a powder, a solution in the hydrophilic polar solvent, or a mixed solution in water and the hydrophilic polar solvent is mixed and stirred.

In the two charging methods described above, the materials to be added later may be entirely added at a time or may be divided and then added, or a solution may be continuously dropped. Divided addition or continuous dropping is preferred.

When the reaction temperature of the reaction is 0° C. to 90° C., [1,1'-binaphthalene]-2,2',7,7'-tetraol is generally produced as a main product, and in order to suppress the production of by-products, the reaction temperature is preferably 0° C. to 60° and more preferably 20° C. to 40° C. The reaction time is 0.5 hours to 10 hours and preferably 1 to 6 hours.

After the reaction, an organic material containing [1,1'-binaphthalene]-2,2',7,7'-tetraol can be separated from an iron salt in an extraction step using a hydrophobic organic solvent.

The organic solvent used in the extraction step is not particularly limited as long as it is a hydrophobic solvent and dissolves [1,1'-binaphthalene]-2,2',7,7'-tetraol, and examples thereof include alcohol solvents such as butanol, isobutanol, and the like; ester solvents such as methyl acetate ethyl acetate, and the like; ketone solvents such as methyl ethyl ketone, and the like; and combination thereof. Ethyl acetate is preferred.

After the extraction step, a step of substituting the extraction solvent with the aromatic organic solvent is required for leading to the purification step of separating [1,1'-binaphthalene]-2,2',7,7'-tetraol dissolved in the aromatic solvent from insoluble substances or the step of separating [1,1'-binaphthalene]-2,2',7,7'-tetraol dissolved in the aromatic solvent from insoluble substances and then heat-concentrating the resultant solution to precipitate a solid of [1,1'-binaphthalene]-2,2',7,7'-tetraol.

In the step of substituting the extraction solvent with the aromatic organic solvent, toluene may be added to the composition product from which the solvent has been removed, and when the extraction solvent has a boiling point lower than that of the aromatic solvent, the aromatic solvent may be added to the extraction solvent, and the extraction solvent may be gradually moved by heating under reflux.

[Curing Agent]

Next, an epoxy resin composition of the present invention contains the novel epoxy compound detailed above and a curing agent, and the epoxy compound may be used as a reaction product containing an oligomer component produced during production.

The curing agent used is not particularly limited, and any compound which is commonly used as a curing agent for usual epoxy resins can be used, and examples thereof include amine compounds, amide compounds, acid anhydride compounds, phenol compounds, and the like. Specific examples of the amine compounds include diaminodiphenylmethane, diethylene triamine, triethylene tetramine, diaminodiphenyl sulfone, isophorone diamine, imidazole, BF3-amine complex, guanidine derivatives, and the like. Examples of the amide compounds include dicyandiamide, polyamide resin synthesized by a linolenic acid dimer and ethylenediamine, and the like. Examples of the acid anhydride compounds include phthalic anhydride, trimellitic anhydride, pyromellitic anhydride, maleic anhydride, tetrahydrophthalic anhydride, methyltetrahydrophthalic anhydride, methylnadic anhydride, hexahydrophthalic anhydride, methylhexahydrophthalic anhydride, and the like. Examples of the phenol compounds include polyhydric phenol compounds such as phenol novolac resins, cresol novolac resins, aromatic hydrocarbon formaldehyde resin-modified phenol resins, dicyclopentadiene phenol-added resins, phenol aralkyl resins (Xyloc resins), polyhydric phenol novolac resins represented by resorcin novolac resins, which are synthesized from polyhydric hydroxyl compounds and formaldehyde, naphthol aralkyl resins, trimethylol methane resins, tetraphenylol ethane resins, naphthol novolac resins, naphthol-phenol condensed novolac resins, naphthol-cresol condensed novolac resins, biphenyl-modified phenol resins (polyhydric phenol compounds in which phenol nuclei are connected through a bismethylene group), biphenyl-modified naphthol resins (polyhydric naphthol compounds in which naphthol nuclei are connected through a bismethylene group), aminotriazine-modified phenol resins (polyhydric phenol compounds in which phenol nuclei are connected with melamine or benzoguanamine through a methylene bond), alkoxy group-containing aromatic ring-modified novolac resins (polyhydric phenol compounds in which phenol nuclei and alkoxy group-containing aromatic rings are connected through formaldehyde), and the like. These curing agents may be used alone or in combination of two or more.

The amounts of the epoxy resin and curing agent mixed in the epoxy resin composition of the present invention are not particularly limited, but in view of the good characteristics of the resultant cured product, the amount of active groups in the curing agent is preferably 0.7 to 1.5 equivalents relative to a total of 1 equivalent of epoxy groups in the epoxy resin.

[Compound/Additive]

If required, the epoxy resin composition of the present invention can be properly combined with a curing accelerator. Various compounds can be used as the curing accelerator, and examples thereof include phosphorus-based compounds, tertiary amines, imidazole, organic acid metal salts, Lewis acids, amine complex salts, and the like.

The epoxy compound of the present invention described above may be singly used as an epoxy resin component in the epoxy resin composition of the present invention, but if required, the epoxy compound of the present invention may be combined with another known common epoxy resin.

As described above, the detailed epoxy resin composition of the present invention is characterized by exhibiting excellent solvent solubility. Therefore, besides the components described above, the epoxy resin composition may be mixed with an organic solvent. Examples of the organic solvent which can be used include ketone solvents such as acetone, methyl ethyl ketone, methyl isobutyl ketone, cyclohexanone, and the like; acetate solvents such as ethyl acetate, butyl acetate, cellosolve acetate, propylene glycol monomethyl ether acetate, carbitol acetate, and the like; carbitol solvents such as cellosolve, butyl carbitol, and the like; aromatic hydrocarbon solvents such as toluene, xylene, and the like; and amide solvents such as dimethylformamide, dimethylacetamide, N-methylpyrrolidone, and the like.

Further, if required, various known common additives such as a filler, a colorant, a flame retardant, a mold release agent, a silane coupling agent, and the like may be added to the epoxy resin composition of the present invention.

Typical examples of the filler include silica, alumina, silicon nitride, aluminum hydroxide, and the like; typical examples of the colorant include carbon black and the like; typical examples of the flame retardant include antimony trioxide and the like; typical examples of the mold release agent include carnauba wax and the like; and typical examples of the silane coupling agent include aminosilane, epoxysilane, and the like.

[Composition]

The epoxy resin composition of the present invention can be produced by uniformly mixing the components described above. The epoxy resin composition of the present invention which contains the epoxy compound of the present invention, the curing agent, and if required, the curing accelerator can be easily formed into a cured product by the same method as a general known method. Examples of the cured product include molded cured products such as a laminate, a casting, an adhesive layer, a coating film, a film, and the like.

The epoxy resin composition of the present invention can be can be used for applications such as a laminated plate resin material, an electric insulation material, a semiconductor encapsulating material, a fiber-reinforced composite material, a coating material, a molding material, materials of a conductive adhesive and other adhesives, and the like.

The epoxy compound of the present invention has a naphthalene skeleton with good heat resistance and high hydrophobicity, a high crosslink density due to tetrafunctionality, and a molecular structure with good symmetry, and thus the cured product thereof can satisfy excellent heat resistance, hydrophobicity, and low coefficient of thermal expansion property. In comparison with a tetrafunctional glycidyl ether of 1,1'-alkylenebis(2,7-dihydroxynaphthalene) having a similar structure to the epoxy compound of the present invention and produced from the reaction product of dihydroxynaphthalene and formaldehyde described in U.S. Pat. No. 3,137,202, the epoxy compound of the present invention does not have an alkylene structure which is relatively weak to a high temperature while maintaining low moisture absorption due to the naphthalene skeleton and low coefficient of thermal expansion property due to the high crosslink density, and thus exhibits excellent heat resistance, low melt viscosity, and good solvent solubility. When the melt viscosity is decreased from 91° C. to 61° C., in addition to improvement in workability, a low-melt-viscosity or liquid epoxy resin composition can be produced, although it is difficult to produce such an epoxy resin composition from a tetrafunctional glycidyl ether of 1,1'-alkylenebis(2,7-dihydroxynaphthalene). For example, when an acid anhydride is used as the curing agent, a tetrafunctional glycidyl ether of 1,1'-alkylenebis(2,7-dihydroxynaphthalene) forms a solid epoxy resin composition, while the epoxy compound of the present invention can produce a liquid epoxy resin composition. In addition, the epoxy compound of the present invention has good solvent solubility, and thus can be preferably used for applications using a solvent, such as an insulating material for a printed circuit board, and the like, and can be used for more applications.

EXAMPLES

The present invention is described in further detail below with reference to examples and comparative examples. Melt viscosity at 150° C., GPC, and MS spectrum were measured under conditions below.

1) Melt viscosity at 150° C.: measured with an apparatus below according to ASTM D4287.
Apparatus name: MODEL CV-1S manufactured by Codex Corporation
Cone: for 10 dPa·s
2) Method for measuring softening point: measured by a ball & ring (B & R) method using glycerin as a heating medium according to JIS K7234.
Apparatus name: ASP-M2 model manufactured by Meitec Corporation
Heating rate: 5/min
3) GPC: Measurement conditions are as follows.
Measuring apparatus: "HLC-8220 GPC" manufactured by Tosoh Corporation
Column: guard column "HXL-L" manufactured by Tosoh Corporation
"TSK-GEL G2000HXL" manufactured by Tosoh Corporation
"TSK-GEL G2000HXL" manufactured by Tosoh Corporation
"TSK-GEL G3000HXL" manufactured by Tosoh Corporation
"TSK-GEL G4000HXL" manufactured by Tosoh Corporation
Detector: RI (differential refractometer)
Data processing: "GPC-8020 model II version 4.10" manufactured by Tosoh Corporation
Measurement condition: column temperature 40° C.
Moving phase: tetrahydrofuran
Flow rate: 1.0 ml/min
Standard: using monodisperse polystyrene below having a known molecular weight according to a measurement manual of "GPC-8020 model II version 4.10".
(Polystyrene Used)
"A-500" manufactured by Tosoh Corporation
"A-1000" manufactured by Tosoh Corporation
"A-2500" manufactured by Tosoh Corporation
"A-5000" manufactured by Tosoh Corporation
"F-1" manufactured by Tosoh Corporation
"F-2" manufactured by Tosoh Corporation
"F-4" manufactured by Tosoh Corporation
"F-10" manufactured by Tosoh Corporation
"F-20" manufactured by Tosoh Corporation
"F-40" manufactured by Tosoh Corporation
"F-80" manufactured by Tosoh Corporation
"F-128" manufactured by Tosoh Corporation
Sample: prepared by filtering with a microfilter a 1.0 mass % tetrahydrofuran solution in terms of resin solid (5.0 μl).
4) NMR: NMR LA300 manufactured by JEOL Ltd.
Solvent: acetone-d6
5) MS: gas chromatography-time-of-flight mass spectrometer JMS-T100GC manufactured by JEOL Ltd.
Ionization mode: FD
Cathode voltage: −10 kV
Emitter current: 0 mA→40 mA [25.6 mA/min.]
Solvent: tetrahydrofuran
Sample concentration: 2%

Example 1

Figure 2:
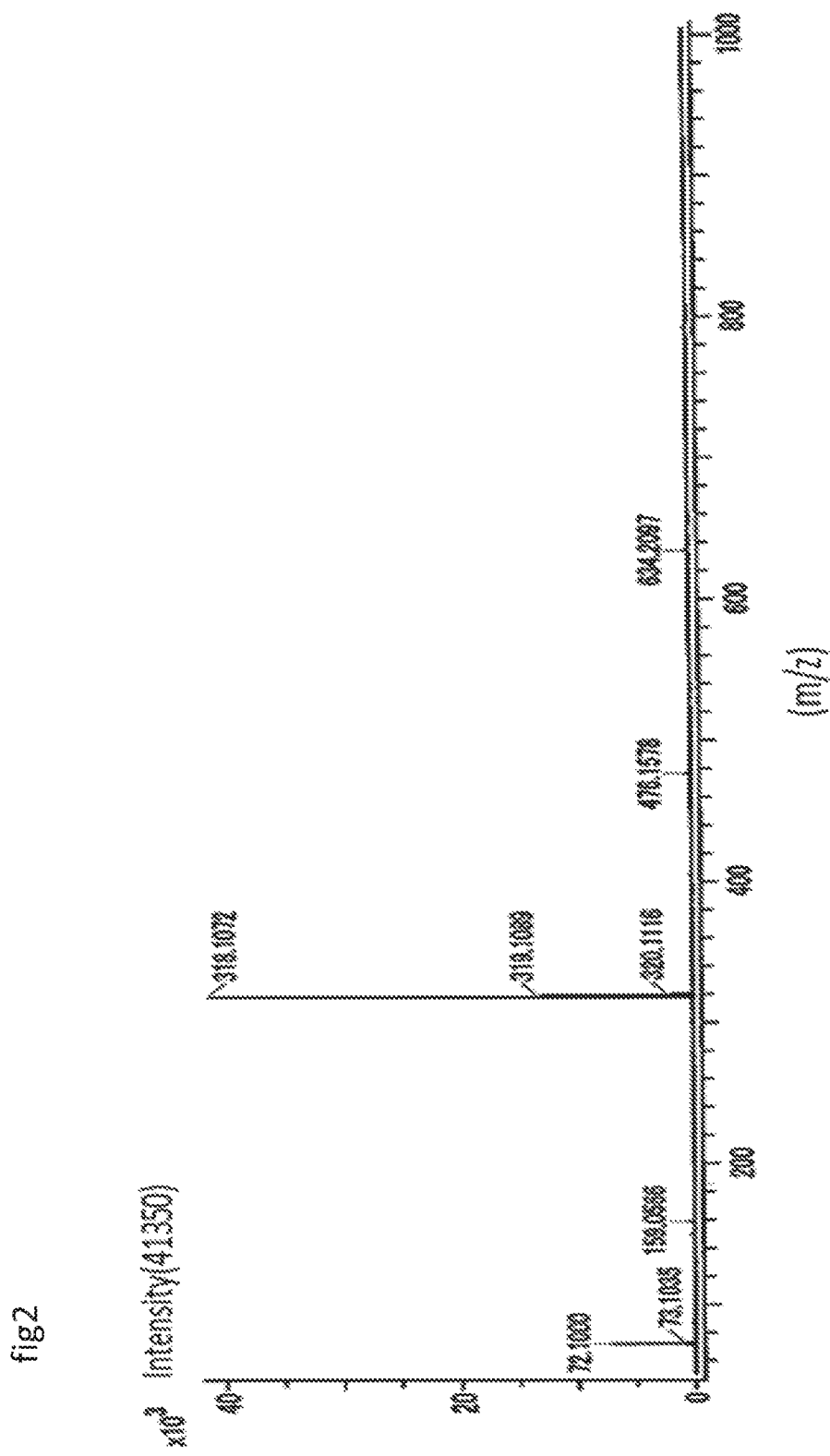
FIG. 2 is a MS chart of [1,1'-binaphthalene]-2,2',7,7'-tetraol produced in Example 1.

In a flask with a thermometer, a stirrer, and a reflux condenser, 139 g (0.5 moles) of iron(III) chloride hexahydrate and 1330 mL of water were charged under nitrogen gas purging, the inside of a reactor was replaced with nitrogen under stirring, and then a solution previously prepared by dissolving 82 g (0.5 moles) of naphthalene-2,7-diol in 190 mL of isopropyl alcohol was added to the reactor, followed by stirring at 40° C. for 30 minutes. A mixed solution of 139 g (0.5 moles) of iron(III) chloride hexahydrate, 664 mL of water, and 94 mL of isopropyl alcohol was added, and the resultant mixture was heated to 40° C. and then further stirred for 1 hour. Then, 500 mL of ethyl acetate was added to the reaction solution and stirred for 10 minutes. The reaction solution was transferred to a separating funnel, an organic layer was separated, and then an aqueous layer was extracted with ethyl acetate. The organic layers were combined and washed with saturated brine. After the solvent was distilled off under vacuum until the amount was about 200 mL, the solution was transferred to a SUS container provided with a thermometer, a stirrer, and Dean-Stark trap, and 5 L of toluene was added. Then, ethyl acetate was evaporated by heating at a temperature lower than the boiling point of toluene, thereby replacing ethyl acetate as the solvent by toluene. The toluene solution was cooled to room temperature, and insoluble substances were filtered off with quantitative filter No. 5C manufactured by Advantec Co., Ltd. The solvent was distilled off from the filtrate under vacuum, and then the residue was dried at 100° C. for 5 hours to produce 66 g (yield 82%) of a solid containing [1,1'-binaphthalene]-2,2',7,7'-tetraol as a main component. FIGS. 1 and 2 show a GPC chart and a MS spectrum chart, respectively, of the resultant compound. In the MS spectrum chart, besides [1,1'-binaphthalene]-2,2',7,7'-tetraol, small amounts of byproducts and naphthalene-2,7-diol used as the raw material were observed in the resultant compound. However, the purity determined by the GPC chart was 98%. In addition, it could be confirmed by differential scanning calorimetry of the compound that the compound is an anhydride having a melting point of 218° C.

Example 2

Figure 3:
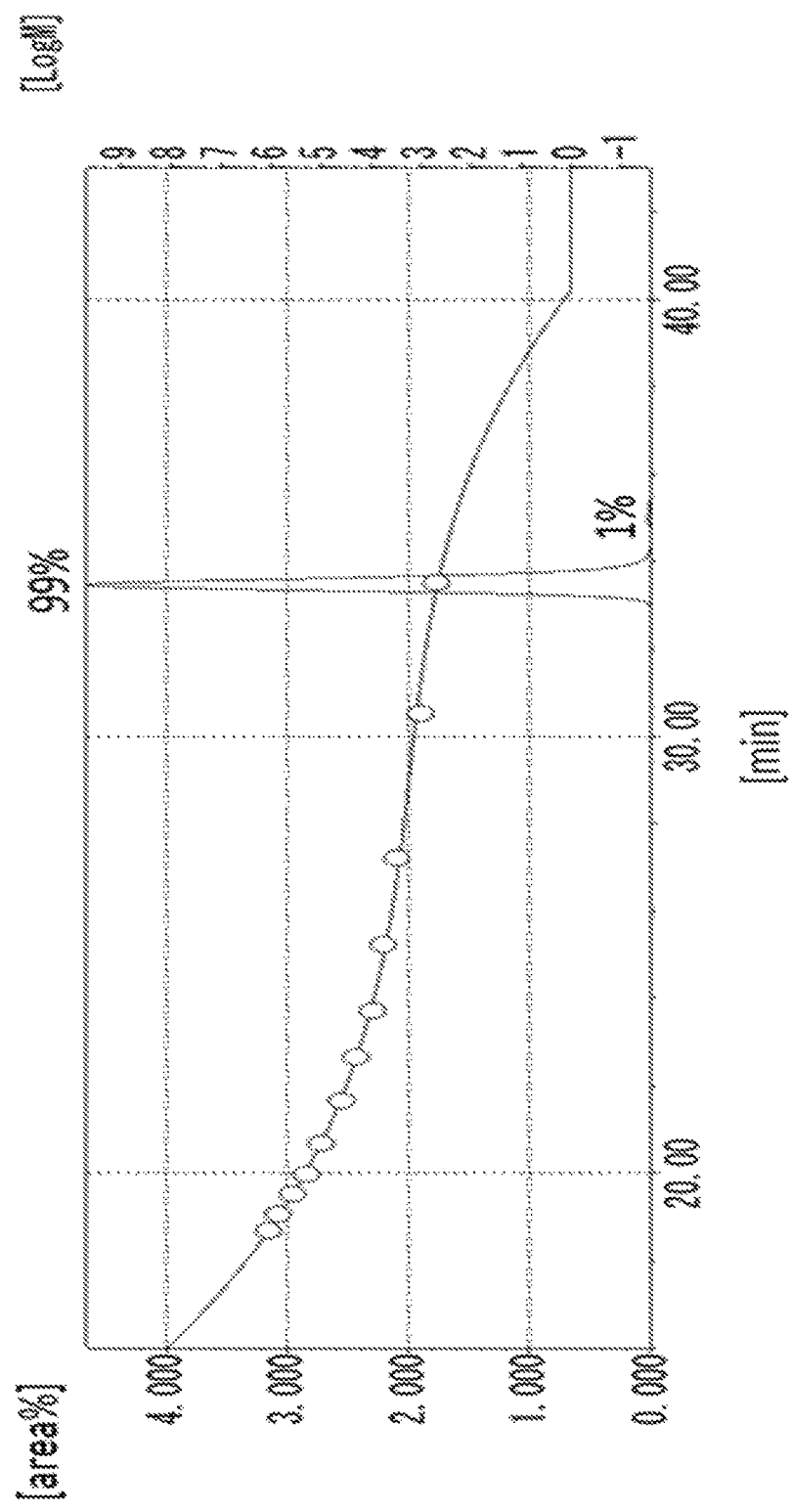
FIG. 3 is a GPC chart of [1,1'-binaphthalene]-2,2',7,7'-tetraol produced in Example 2.
Figure 4:
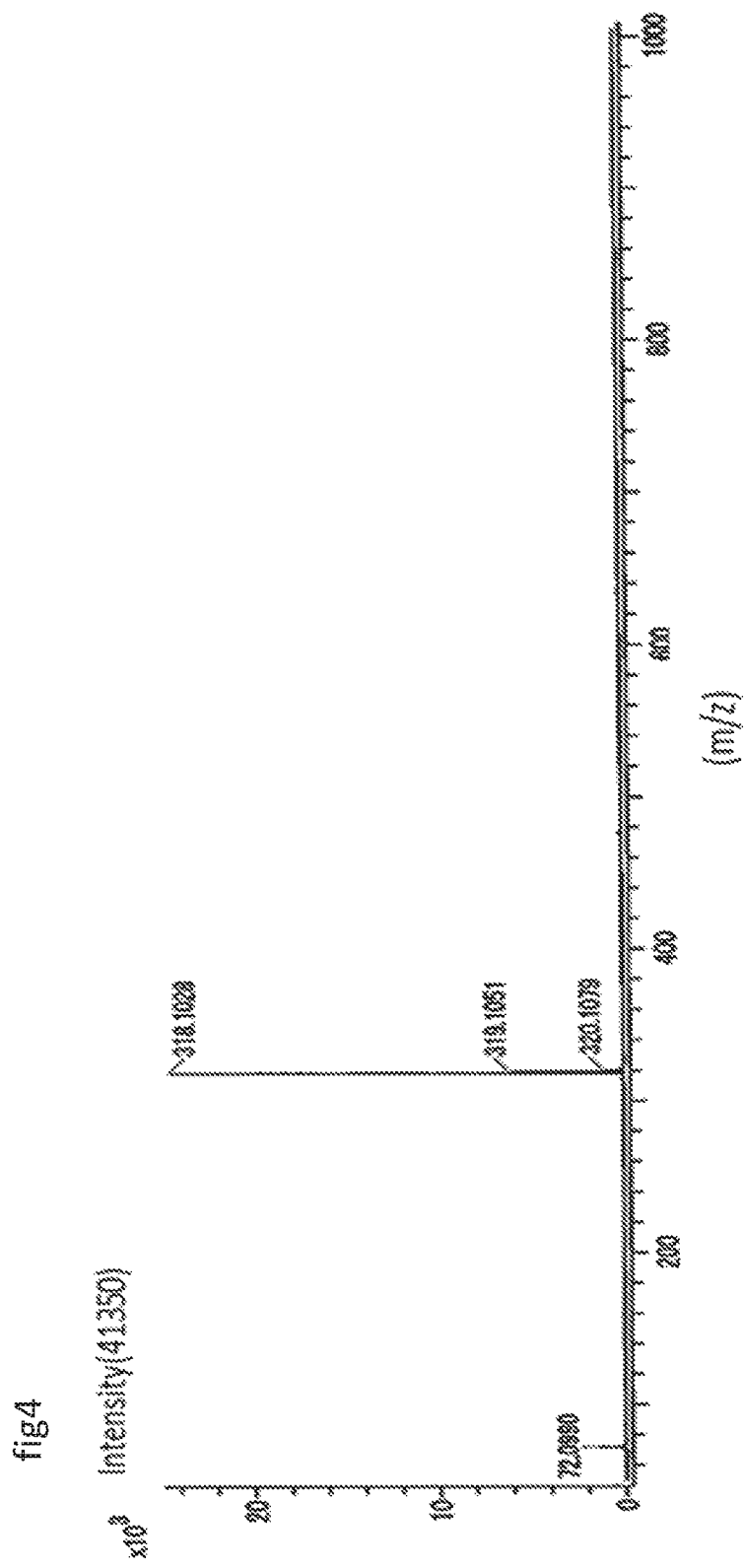
FIG. 4 is a GPC chart of [1,1'-binaphthalene]-2,2',7,7'-tetraol produced in Example 2.

Oxidative coupling reaction, solvent extraction, and solvent replacement were performed under the same conditions as in Example 1, the toluene solution was cooled to room temperature, and insoluble substances were filtered off. The filtrate was transferred to a SUS container provided with a thermometer, a stirrer, and Dean-Stark trap and the filtrate was concentrated by distilling off toluene until the amount was about 500 mL by heating to a temperature higher than the boiling point under stirring, thereby precipitating crystals of [1,1'-binaphthalene]-2,2',7,7'-tetraol. The precipitate and the solvent were hot-filtered at a temperature of 80° C. or more, and the precipitate was dried at 110° C. for 5 hours to produce 53 g (yield 68%) of [1,1'-binaphthalene]-2,2',7,7'-tetraol. FIGS. 3 and 4 show a GPC chart and a MS spectrum chart, respectively, of the resultant compound. The MS spectrum chart indicates that the resultant compound is a single compound of [1,1'-binaphthalene]-2,2',7,7'-tetraol, and the purity determined by the GPC chart was 99%. In addition, it could be confirmed by differential scanning calorimetry of the compound that the compound is an anhydride having a melting point of 218° C.

Example 3

Oxidative coupling reaction and solvent extraction were performed under the same conditions as in Example 1. Then, ethyl acetate was distilled off under vacuum, benzene was added to the resultant crude product, and the mixture was transferred to a SUS container provided with a thermometer, a stirrer, and Dean-Stark trap. Further, benzene was added so that the total amount was 5 L, followed by reflux. The benzene solution was cooled to room temperature, and then insoluble substances were filtered off. The solvent of the filtrate was distilled off under vacuum, and the residue was dried at 110° C. for 5 hours to produce 70 g (yield 87%) of a solid containing [1,1'-binaphthalene]-2,2',7,7'-tetraol as a main component. The purity determined by a GPC chart of the resultant compound was 97%.

Example 4

Oxidative coupling reaction and solvent extraction were performed under the same conditions as in Example 1. Then, the solvent was distilled off under vacuum until the amount was about 200 mL, and the solution was transferred to a SUS container provided with a thermometer, a stirrer, and Dean-Stark trap. Further, 5 L of xylene was added, and then ethylene acetate as the solvent was replaced by xylene. The solution was cooled to room temperature, and then insoluble substances were filtered off. The solvent of the filtrate was distilled off under vacuum, and the residue was dried at 110° C. for 5 hours to produce 68 g (yield 84%) of a solid containing [1,1'-binaphthalene]-2,2',7,7'-tetraol as a main component. The purity determined by a GPC chart of the resultant compound was 98%.

Example 5

In a flask with a thermometer, a stirrer, and a reflux condenser, 50 g of [1,1'-binaphthalene]-2,2',7,7'-tetraol ground with a mortar and 100 g of water were charged and stirred at 60° C. for 30 minutes. The resultant suspension was filtered, and the residue was dried at 90° C. for 5 days to produce 52 g of [1,1'-binaphthalene]-2,2',7,7'-tetraol monohydrate (yield 99%). It was confirmed by differential scanning calorimetry of the resultant compound that the compound has a melting point of 220° C. and a softening point near 124° C., and an exothermic peak at 185° C. corresponding to release of crystal water confirmed that the compound is a monohydrate.

Comparative Example 1

Oxidative coupling reaction and solvent extraction were performed under the same conditions as in Example 1, and ethyl acetate was distilled off under vacuum. As a result of MS analysis of the crude product, it was found that the crude product is a mixture of [1,1'-binaphthalene]-2,2',7,7'-tetraol, the raw material, multimers, and other byproducts, and the purity in the molecular weight region of 1,1'-binaphthalene]-2,2',7,7'-tetraol determined by a peak area of a GPC chart was 76%.

Comparative Example 2

Oxidative coupling reaction and solvent extraction were performed under the same conditions as in Example 1. Ethyl acetate was distilled off under vacuum, and then ethanol was added to the resultant crude product. The mixture was transferred to a SUS container provided with a thermometer, a stirrer, and Dean-Stark trap, and ethanol was further added so that the total amount was 500 mL, followed by reflux. The ethanol solution was cooled to room temperature, and then insoluble substances were filtered off. The solvent of the filtrate was distilled off under vacuum, and the residue was dried at 110° C. for 5 hours to produce 80 g (yield 99%) of a solid containing [1,1'-binaphthalene]-2,2',7,7'-tetraol as a main component. The purity determined by a GPC chart of the resultant compound was 77%.

Comparative Example 3

Oxidative coupling reaction and solvent extraction were performed under the same conditions as in Example 1. Ethyl acetate was distilled off under vacuum, and then hexane was added to the resultant crude product. The mixture was transferred to a SUS container provided with a thermometer, a stirrer, and Dean-Stark trap, and hexane was further added so that the total amount was 5 L, followed by reflux. The hexane solution was cooled to room temperature, and then insoluble substances were filtered off. The solvent of the filtrate was distilled off under vacuum, and the residue was dried at 110° C. for 5 hours to produce 2 g (yield 3%) of a solid containing [1,1'-binaphthalene]-2,2',7,7'-tetraol as a main component. 1,1'-Binaphthalene]-2,2',7,7'-tetraol was difficult to separate from impurities because of its low solubility in hexane.

Comparative Synthesis Example 1

In a flask with a thermometer, a stirrer, and a reflux condenser, 139 g (0.5 moles) of iron(III) chloride hexahydrate and 1330 mL of water were charged under nitrogen gas purging, the inside of a reactor was replaced with nitrogen under stirring, and then a solution previously prepared by dissolving 82 g (0.5 moles) of naphthalene-1,6-diol in 190 mL of isopropyl alcohol was added to the reactor, followed by stirring at 40° C. for 1 hour. Then, 500 mL of ethyl acetate was added to the reaction solution and stirred for 10 minutes. The reaction solution was transferred to a separating funnel, an organic layer was separated, and an aqueous layer was further extracted with ethyl acetate. The combined organic layers were washed with saturated brine and concentrated under vacuum. The resultant product was a mixture of a dimer, a trimer, and a tetramer, and each of these multimers was a complicated mixture containing naphthalene bonding at the 1,1'-positions and at other positions. Therefore, the dimer could not be separated with high purity and was not suitable as a raw material of epoxy resins. This result indicates the importance of the positions of hydroxyl groups in dihydroxynaphthalene.

Example 6

In a flask with a thermometer, a stirrer, and a reflux condenser, 139 g (0.5 moles) of iron(III) chloride hexahydrate and 1330 mL of water were charged under nitrogen gas purging, the inside of a reactor was replaced with nitrogen under stirring, and then a solution previously prepared by dissolving 82 g (0.5 moles) of 2,7-dihydroxynaphthalene in 190 mL of isopropyl alcohol was added to the reactor, followed by stirring at 40° C. for 30 minutes. A mixed solution of 139 g (0.5 moles) of iron(III) chloride hexahydrate, 664 mL of water, and 94 mL of isopropyl alcohol was added, and the resultant mixture was heated to 40° C. and then further stirred for 1 hour. Then, 500 mL of ethyl acetate was added to the reaction solution and stirred for 10 minutes. The reaction solution was transferred to a separating funnel, an organic layer was separated, and then an aqueous layer was extracted with ethyl acetate. The organic layers were combined and washed with saturated brine. After the solvent was distilled off under vacuum until the amount was about 200 mL, the solution was transferred to a SUS container provided with a thermometer, a stirrer, and Dean-Stark trap, and 5 L of toluene added. Then, ethyl acetate and water as the solvent were replaced by toluene. The toluene solution was cooled to room temperature, and insoluble substances were filtered off. The filtrate was transferred to a SUS container provided with a thermometer, a stirrer, and Dean-Stark trap and the filtrate was concentrated by distilling off the toluene until the amount was about 500 mL by heating to a temperature higher than the boiling point under stirring, thereby precipitating crystals of [1,1'-binaphthalene]-2,2',7,7'-tetraol. The precipitate and the solvent were hot-filtered at a temperature of 80° C. or more, and then the precipitate was dried at 110° C. for 5 hours to produce 53 g (yield 68%) of [1,1'-binaphthalene]-2,2',7,7'-tetraol. It was confirmed by GPC and MS that the resultant [1,1'-binaphthalene]-2,2',7,7'-tetraol has high purity without containing multimerized components.

Figure 5:
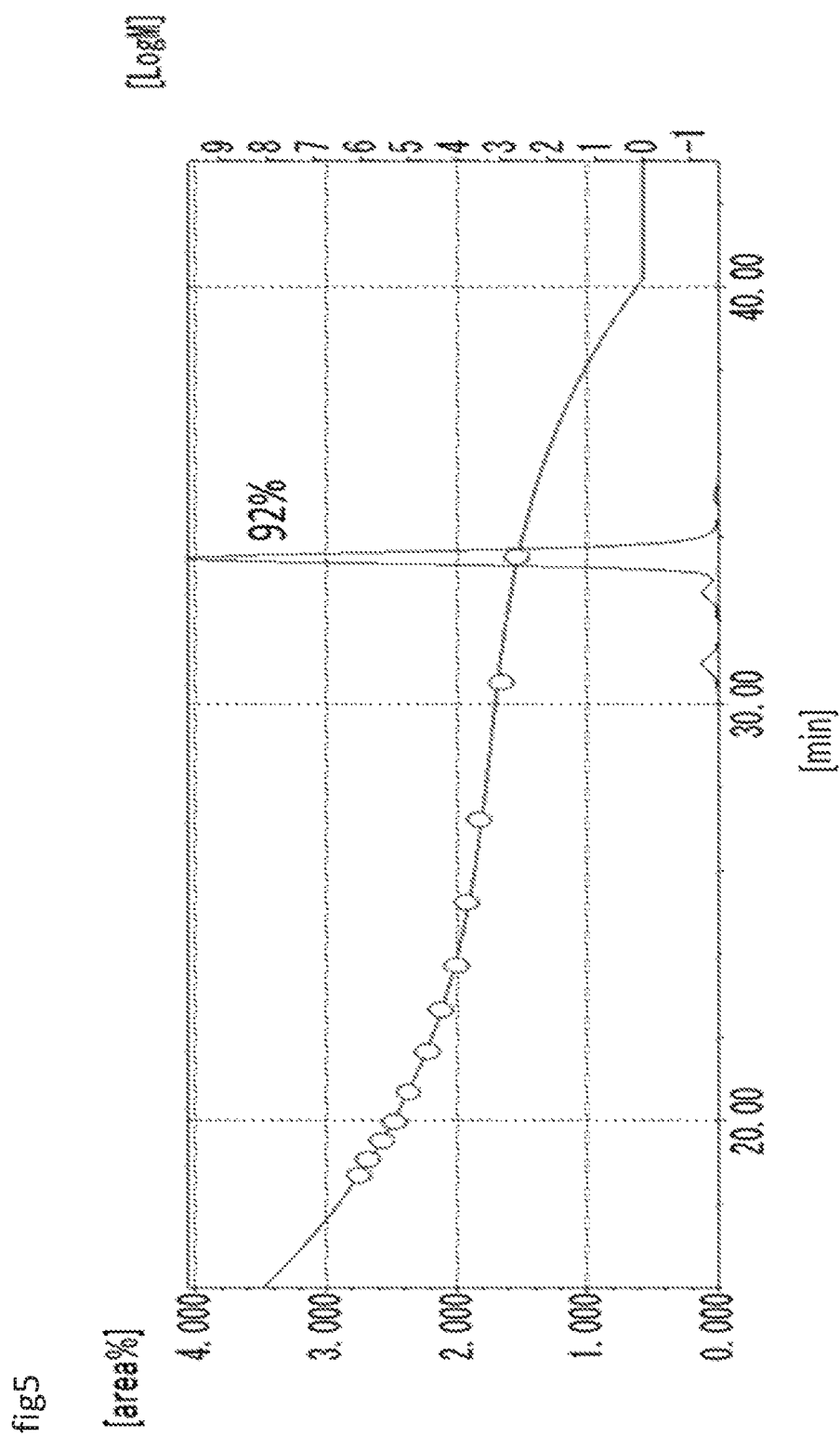
FIG. 5 is a GPC chart of Example 6.
Figure 6:
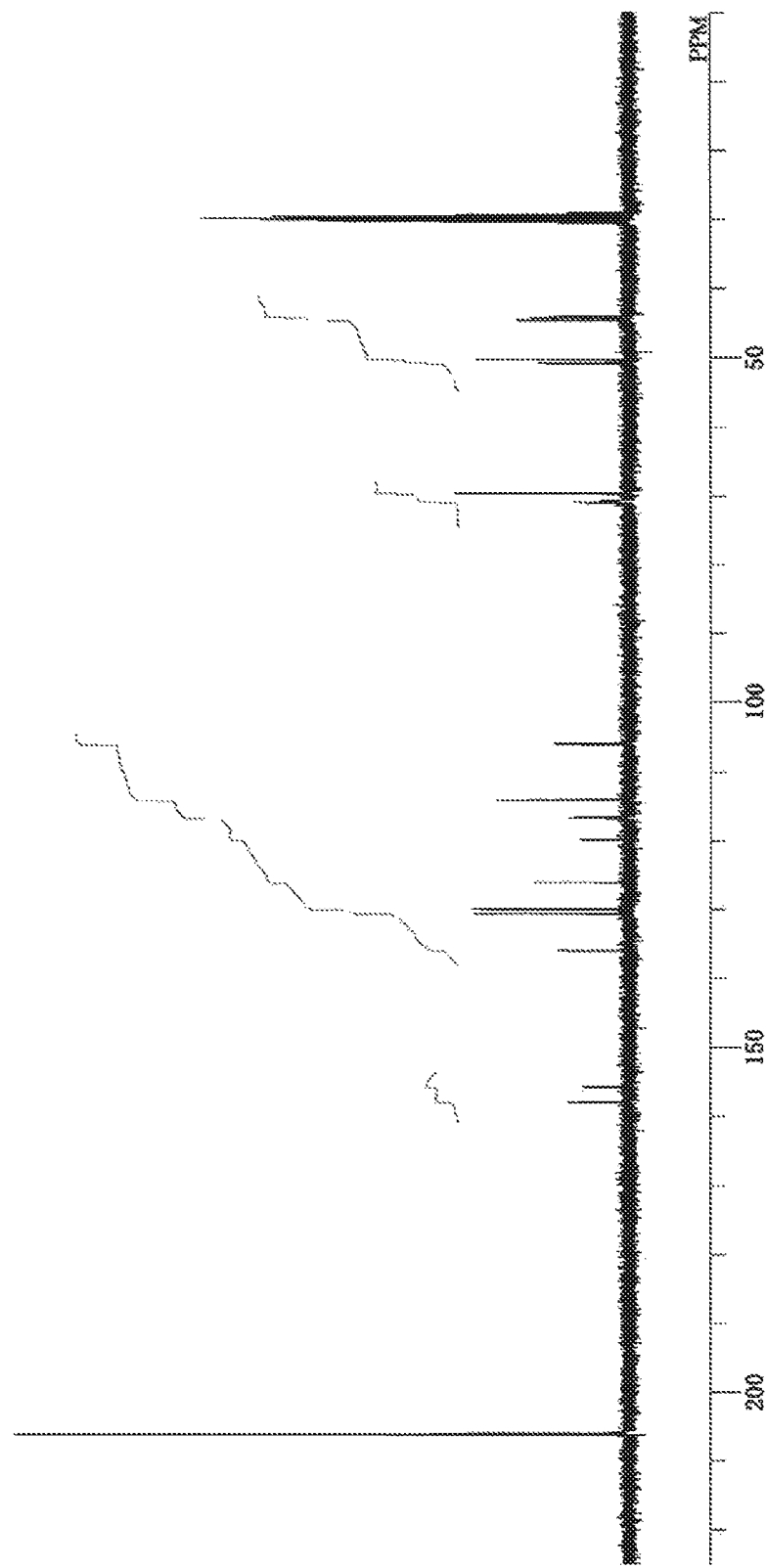
FIG. 6 is a NMR chart of Example 6.

In a flask with a thermometer, a dropping funnel, a cooling tube, and a stirrer, 79.5 g (0.25 moles) of [1,1'-binaphthalene]-2,2',7,7'-tetraol synthesized by the method described above, 462 g (5.0 moles) of epichlorohydrin, and 126 g of n-butanol were charged and dissolved. The temperature was increased to 40° C., and then 100 g (1.20 moles) of a 48% aqueous sodium hydroxide solution was added to the resultant solution over 8 hours. Then, the temperature was further increased to 50° C., and reaction was further performed for 1 hour. After the finish of the reaction, 150 g of water was added, the resultant mixture was allowed to stand, and then a lower layer was discarded. Then, unreacted epichlorohydrin was distilled off at 150° C. under reduced pressure. Then, 230 g of methyl isobutyl ketone was added to the resultant crude epoxy resin to prepare a solution. Further, 100 g of a 100 mass % aqueous sodium hydroxide solution was added to the solution, subjected to reaction at 80° C. or 2 hours, and then repeatedly washed with water three times until the washing solution showed neutral pH. Next, the system was dehydrated by azeotropy, and the solvent was distilled off under reduced pressure after microfiltration, thereby producing 135 g of a target resin, 2,2',7,7'-tetraglycidyloxy-[1,1'-binaphthalene] (A-1). The resultant epoxy resin (A-1) had a softening point of 61° C. (B & R method), a melt viscosity of 1.1 dPa·s (measurement method: ICI viscometer method, measurement temperature: 150° C.), and an epoxy equivalent of 144 g/equivalent. FIG. 5 shows a GPC chart of the epoxy resin, FIG. 7 shows a C13 NMR chart, and FIG. 6 shows a MS spectrum. In the MS spectrum, a peak at 542 showing 2,2'7,7'-tetraglycidyloxy-[1,1'-binaphthalene] (A-1) was observed.

Example 7 and Comparative Example 4

Each of the epoxy resin (A-1) of the present invention produced in Example 6 and a comparative epoxy resin (A-2) [a tetrafunctional naphthalene epoxy resin represented by a structural formula below ("Epiclon HP-4700" manufactured by DIC Corporation, softening point 91° C., 150° C. melt viscosity 4.5 ps, epoxy equivalent 166 g/eq)],

[Chem. 3]

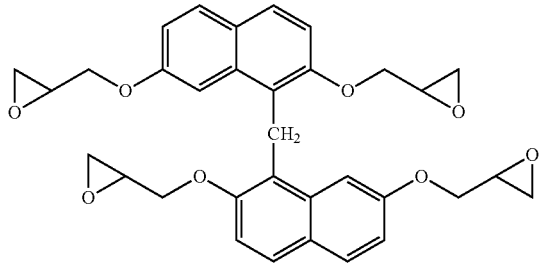

a phenol novolac-type phenol resin ("Phenolite TD-2131" manufactured by DIC Corporation, hydroxyl equivalent 104 g/eq) serving as a curing agent, and triphenylphosphine (TPP) serving as a curing accelerator were mixed according to a composition shown in Table 1. The mixture was flowed into a mold of 11 cm×9 cm×2.4 mm and molded by a press at a temperature of 150° C. for 10 minutes. Then, the molded product was removed from the mold and cured at a temperature of 175° C. for 5 hours to form a cured product. The cured product was evaluated with respect to heat resistance, coefficient of linear expansion, and moisture absorptivity. Also, the solvent solubility of each of the epoxy resin (A-1) and the epoxy resin (A-2) was measured by a method described below. The results are shown in Table 1.

<Heat Resistance (Glass Transition Temperature: Tg (DMA)>

A temperature at which a change in elastic modulus was maximized (the highest rate of change in tan δ) was evaluated as the glass transition temperature by using a viscoelasticity measuring apparatus (DMA: Rheometrics Inc., solid viscoelasticity measuring apparatus RSA II, rectangular tension method: frequency 1 Hz, heating rate 3° C./min).

<Heat Resistance (5%-Weight-Loss Temperature)

A resin coating film was weighed in an aluminum pan vessel and heated from room temperature to 500° C. to measure a 5%-weight-loss temperature by using a simultaneous thermogravity-differential scanning calorimetry measuring apparatus (TG/DTA6200 manufactured by SII Nanotechnology Inc.)

Measurement Conditions
Measurement temperature; room temperature to 500° C.
Measurement atmosphere: nitrogen
Heating rate: 10° C./min <Coefficient of Linear Expansion>

Thermomechanical analysis was performed in a compression mode by using a thermomechanical analyzer (TMA: SS-6100 manufactured by Seiko Instruments Inc.).

Measurement Conditions
Measurement load; room 88.8 mN
Heating rate: two times at 3° C./min
Measurement temperature range: −50° C. to 300° C.

Measurement was performed two times for a same sample, and a mean coefficient of expansion within a temperature range of 25° C. to 280° C. in the second measurement was evaluated as a coefficient of linear expansion.

<Moisture Absorptivity>

A moisture absorption rate was calculated from a rate of weight increase after moisture absorption for 300 hours in a constant-temperature constant-humidity apparatus under moisture absorption conditions of 85° C. and 85% RH.

<Solvent Solubility>

In a sample bottle, 10 parts of epoxy resin was dissolved in 4.3 parts of methyl ethyl ketone in a closed state at 60° C. Then, the solution was cooled to 25° C., and whether or not crystals were precipitated was evaluated. When crystals were not precipitated, solvent solubility was determined as "Good", and when crystals were precipitated, solvent solubility was determined as "Poor".

TABLE 1

|  |  | Example 7 | Comparative Example 4 |
|---|---|---|---|
| Epoxy resin | A-1 | 46.5 |  |
|  | A-2 |  | 49.2 |
| Curing agent | TD-2131 | 33.5 | 30.8 |
| TPP |  | 0.8 | 0.8 |
| Softening point of epoxy resin (° C.) |  | 61 | 91 |
| Melt viscosity at 150° C. of epoxy resin (° C.) |  | 1.1 | 4.5 |
| Tg (DMA) |  | 248 | 237 |
| 5% weight-loss temperature (° C.) |  | 387 | 378 |
| Coefficient of linear expansion (ppm) |  | 84 | 87 |
| Moisture absorptivity |  | 2.14 | 2.20 |
| Solvent solubility |  | Good | Poor |

The results shown in Table 1 indicate that the epoxy compound of the present invention has a low softening point and low melt viscosity, and a cured product thereof has good solvent solubility and excellent heat resistance while maintaining a low moisture absorptivity and low coefficient of thermal expansion which are characteristic of naphthalene-based tetrafunctional epoxy compounds.

INDUSTRIAL APPLICABILITY

An epoxy compound, an epoxy resin composition, and a cured product of the present invention can be preferably used for applications such as a laminated plate resin material, an electric insulating material, a semiconductor encapsulating material, a fiber-reinforced composite material, a coating material, a molding material, materials of a conductive adhesive and other adhesive, etc.

The invention claimed is:

1. An epoxy resin composition consisting essentially of an epoxy compound and a curing agent; wherein the epoxy compound is 2,2',7,7'-tetraglycidyloxy-1,1'-binaphthalene.

2. A cured product produced by curing the epoxy resin composition according to claim 1.

3. An epoxy resin composition consisting essentially of an epoxy compound and a curing agent; wherein the epoxy compound is produced by a method comprising reacting [1,1'-binaphthalene]-2,2',7,7'-tetraol or its monohydrate with epihalohydrin.

4. A cured product produced by curing the epoxy resin composition according to claim 3.

* * * * *